United States Patent [19]
Gross et al.

[11] 4,076,426
[45] Feb. 28, 1978

[54] METHOD FOR INSPECTING CATHODE-RAY-TUBE WINDOW FOR OBJECTIONABLE CORD

[75] Inventors: Harvey Andrew Gross, Circleville, Ohio; Harry Robert Frey; John David Messner, both of Lancaster, Pa.; Raymond Frederick Walters, Columbus, Ohio

[73] Assignee: RCA Corporation, New York, N.Y.

[21] Appl. No.: 700,892

[22] Filed: Jun. 29, 1976

[51] Int. Cl.² .......................................... G01N 21/16
[52] U.S. Cl. ................................................ 356/239
[58] Field of Search ...................... 356/120, 237, 239

[56] References Cited

U.S. PATENT DOCUMENTS 3,185,022   5/1965   Holeman .................... 356/120 X

FOREIGN PATENT DOCUMENTS 1,245,488   9/1960   France ....................... 356/237

Primary Examiner—John K. Corbin
Assistant Examiner—Matthew W. Koren
Attorney, Agent, or Firm—G. H. Bruestle; L. Greenspan

[57] ABSTRACT

In inspecting a cathode-ray-tube window having a light-scattering inner surface, a pattern, which approximates the structure of the video images to be viewed through the window, is placed close to or against the inner surface. The pattern is observed through the window, and those local regions where the pattern appears to be distorted are identified.

9 Claims, 5 Drawing Figures

METHOD FOR INSPECTING CATHODE-RAY-TUBE WINDOW FOR OBJECTIONABLE CORD

BACKGROUND OF THE INVENTION

This invention relates to a novel method for inspecting glass viewing windows for cathode-ray tubes to detect objectionable cords; and particularly to such a method as would permit those viewing windows with objectionable cords to be identified at the glass factory or at incoming parts inspection at the tube-making factory. "Cords" are minor variations of the index of refraction in localized regions of the window.

A cathode-ray tube, such as a television picture tube, usually comprises a glass window and a luminescent viewing screen supported on the inner surface of the window. Video images are generated on the screen as an array of video image elements and are viewed through the window. The video image elements are small, light-emitting areas of the screen of similar size which are arranged in a repetitive array. There are normally hundreds of thousands of such elements on the screen. In positive-tolerance, shadow mask tubes, the elements are defined by the size and shape of the electron beam spots impinging on the screen. In negative-tolerance, shadow mask tubes, the elements are defined by the size and shape of the holes in the light-absorbing matrix between the viewing screen and the glass window. The inner surface of the window is stippled for reasons related to the fabrication of the window and/or of the screen. The stippled finish has the effect of scattering light which passes through it.

As fabricated, glass viewing windows for cathode-ray tubes have cords present to a greater or lesser degree. Cords are within the thickness of the glass and can occur at different distances from the inner surface of the window. Cords usually result from minor variations in glass composition, although other causes are possible. Cords are transparent and do not produce a change in color or opacity where they occur. However, the minor variations in index of refraction which are characteristic of cords may cause the viewed video image to be distorted at localized regions of the window. These distortions are particularly objectionable where the change in index of refraction is relatively sharp, relatively large, and the boundary of the cord parallels or nearly parallels the alignment of the video image elements of the viewed image. In many cases, as where the boundary of the cord crosses the alignment of the image elements at greater angles than near parallel, the presence of cords is not objectionable, even where the transition is large and/or sharp. The alignment of image elements as used herein refers to the visual effect of orderly rows of elements in a specific direction or directions in a repetitive array of elements.

In some prior methods of inspecting viewing windows for cords, a white background is pressed against the inner surface of the window, bright light is projected through the window onto the white background and the inspector observes the background through the window looking for variations in brightness caused by cords, called "shadows," which are cast on the background. The inspector moves his eyes to different positions and angles with respect to the glass surface, hoping to find the cords. Some inspectors become quite skilled at this. But, even under the best of conditions and with superior skill, cords are difficult to detect because the glass is transparent at and around the boundary of a cord, where there is only a transition of the refractive indices. The task is made more difficult due to the presence of the light-scattering finish on the inner surface of the window, which blurs the "shadows" caused by the cords; and due to the usual presence of a gray tint in the glass to reduce the light transmission through the window, which makes the "shadows" more difficult to see.

SUMMARY OF THE INVENTION

The novel method for inspecting cathode-ray-tube windows having a light-scattering inner surface comprises providing a pattern of visually contrasting areas, which pattern approximates the structure of the array of video image elements to be viewed through the window. The pattern is positioned adjacent, and preferably against, the inner surface of the window, and the pattern is viewed through the window. Those local regions of the viewed pattern which appear distorted are identified as having objectionable cord. Those local regions which have cord but do not distort the viewed pattern are not identified as objectionable.

The method may be implemented with a minimum of equipment, skill and labor and is adaptable to mass-production techniques in both the glass-making factory prior to shipping and the tube-making factory at incoming-materials inspection. The novel method is not only faster than prior methods of inspecting for cords, but also ignores cords (i.e. permits them to pass inspection) which are not objectionable from the viewer's standpoint.

DETAILED DESCRIPTION OF THE PREFERRED EMBODIMENTS

Figure 1:
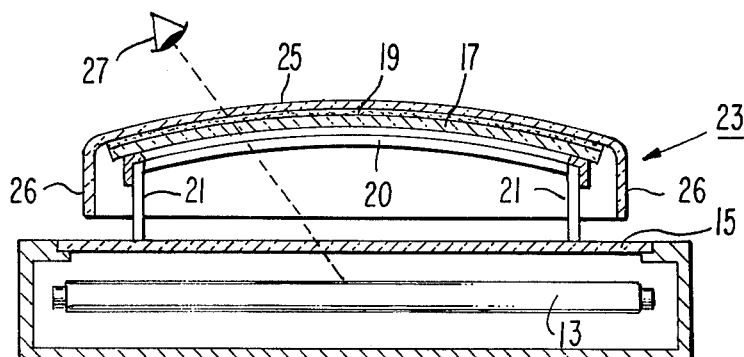
FIG. 1 is a partially-schematic, sectional view of an apparatus for practicing the novel method.
Figure 2:
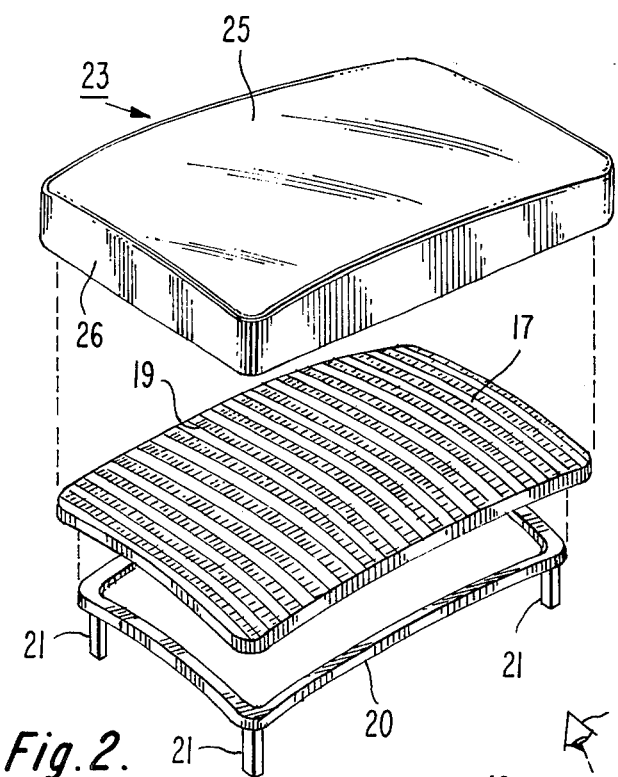
FIG. 2 is an exploded perspective view of the pedestal and panel shown in FIG. 1.

The novel inspection method may be practiced as a table-top operation performed in a booth to shield the equipment and the operator, at least partially, from normal ambient lighting. As shown in FIGS. 1 and 2, the equipment includes a diffuse-light source and a translucent pedestal thereon. The light source shown is a shallow box 11 enclosing several fluorescent lamps 13 set in a parallel array. The upper wall 15 (as shown) of the light box 11 is a translucent plastic plate. With this arrangement, diffuse light passes upwards out of the box 11.

The pedestal 17 is a translucent plastic plate that carries a pattern 19 (hereinafter described) on its upper surface (as shown). The upper surface of the plastic plate constituting the pedestal 17, which carries the pattern 19, has the shape of the inner surface of the window to be inspected. The pedestal 17 is supported on a rectangular frame 20 which has four legs 21, one in each corner of the frame 20, that rests on and is preferably physically attached to the upper wall 15 of the light box 11. The pedestal 17 is of such length and width that it fits within the faceplate and overlies the entire image viewable portion thereof, but may be smaller and overlie much less than the full viewable window surface.

To practice the method with the above-described apparatus, a faceplate panel 23 is placed over the pedestal 17, with the inner surface of the window 25 of the panel 23 in physical contact with the pattern 19 and the sidewalls 26 extending downward. Diffuse light from the lamps 13 passing through the upper wall 15 and the pedestal 17 illuminates the pattern 19, which is a repetitive array of visually-contrasting areas. An inspector, indicated by a symbolic eye 27, views the pattern 19 through the window 25 looking for areas of optical confusion, pattern distortion, and moire. If no such areas are observed, then no objectionable cords are present; although there may be cords present. Objectionable cords will be displayed as an easily-observed beat pattern, and the area can be marked, as with a glassmarking pencil, and may be rejected for further processing.

Figure 3:
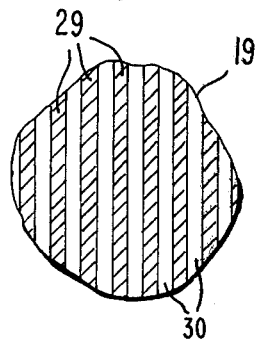
FIG. 3 is a broken-away plan view of a line pattern that may be used in the equipment shown in FIG. 1.

One feature of the novel method is that only objectionable cords are displayed, thereby permitting windows with nonobjectionable cords to be retained for further processing. This is achieved by matching the structure of the pattern 19 in the apparatus to the elemental structure of the video image which will ultimately be displayed on a screen on that window. The pattern 19, shown in greater detail in FIG. 3, is a repetitive array of black stripes 29 spaced by clear areas 30. Such a pattern of stripes would be used to inspect windows that would ultimately carry a luminescent screen comprised of stripes of luminescent material running in the same direction. Such a screen could also carry black, light-absorbing stripes between the stripes of luminescent material. Such light-absorbing stripes are sometimes called guard bands or a black matrix or a black surround. The pattern used in the novel method may be substantially identical to such light-absorbing stripes.

Figure 4:
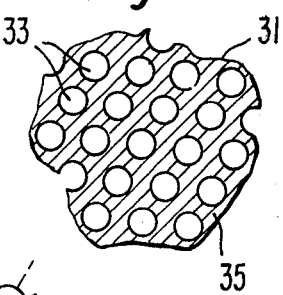
FIG. 4 is a broken-away plan view of a dot pattern that may be used in the equipment shown in FIG. 1.

The stripe pattern on the pedestal 17 should closely approximate the elemental structure of the screen which is later supported there with respect to the widths and pitch of the stripes. The video image elements displayed thereon will follow closely that geometry. Some luminescent screens include bridges between the stripes. It has been found that it is not necessary to include such bridges or other fine detail in the pattern 19. In one suitable pattern, the opaque stripes were 4 to 6 mils wide on 10-mil centers.

Where the window is to be used to support a luminescent screen comprised of a hexagonal array of luminescent dots, with or without light-absorbing material or matrix or surround, the pattern will similarly approximate the structure of the video image elements displayed on that screen. For negative-tolerance tubes, where a black matrix defines the video image elements, the pattern may be substantially identical to that matrix. The pattern 31 shown in FIG. 4 is exemplary of a pattern for inspecting windows for use with dot screens. The pattern 31 includes dot-like light-transmitting areas 33 spaced by opaque material 35. The size and spacing of the dot-like areas closely approximate the size and spacing of the luminescing spots in the screen to be supported by the window.

Figure 5:
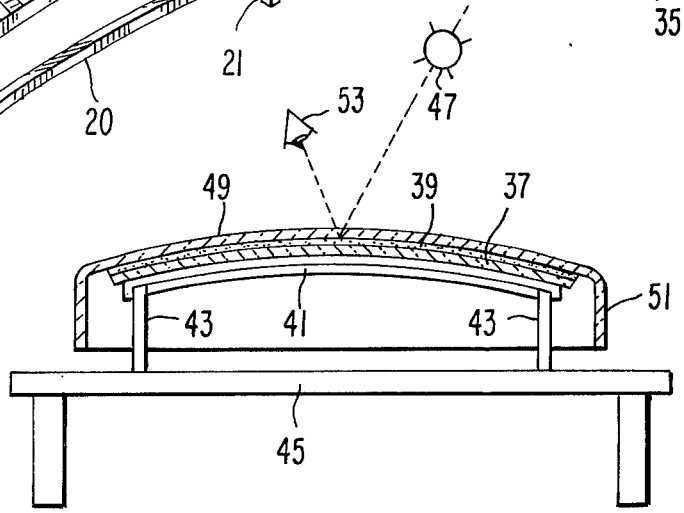
FIG. 5 is a partially-schematic sectional view of another apparatus that may be used for practicing the novel method.

An alternate system of practicing the novel method is shown in FIG. 5. In this apparatus, a pedestal 37 comprising a supporting plate carrying a pattern 39 is mounted on a frame 41 having four legs 43, as shown in FIG. 2. The pedestal 37 rests on a table 45. Unlike the equipment of FIG. 2, a diffuse light source 47 is positioned above and at an angle to the upper surface of the pedestal 37. A panel is placed over the pedestal 37 with the inner surface of the window 49 against the pattern 39 and with the sidewalls 51 of the panel extending downwards. An inspector, shown symbolically by an eye 53, views the pattern 39 through the window 49 in the reflected light from the source 47, looking for areas of optical confusion, moire, and pattern distortion, as described above. This alternate method of viewing the pattern in reflected, instead of transmitted, light is not preferred because the areas of the pattern are not as well contrasted to the inspector. In both cases, cords are viewable, and the observation is aided by the movement of the inspector with respect to the assembly.

Another factor of considerble importance is the spacing of the pattern from the inside surface of the window. The preferred relationship is with the pattern in physical contact with the inside window surface, although good optical contact is not necessary. The pattern, however, can be spaced a small distance from the inner window surface up to about 4.0 millimeters. The inner window surface is stippled, or otherwise light scattering. The average maximum peak and valley of such stipple is typically 15 microinches. The smaller the spacing of the pattern from the surface, the better the resolution of the viewed pattern.

In the methods exemplified by FIGS. 1 and 5, the pattern is placed adjacent the inner side of the window and is viewed through the window from the outer side thereof. A pattern placed adjacent the outer side of the window cannot be viewed from the inner side because the light-scattering inner surface interferes with such viewing arrangement.

The pattern can be supported and brought into contact with the inner window surface with other means. For example, the pattern could be supported on a sponge or other compliant structure so that the weight of the panel forces the pattern to conform to the window surface. Alternatively, the pattern can be supported on a flexible support that is part of an inflatable chamber. In that structure, the window is positioned opposite the pattern and the chamber inflated to press the pattern against the inside window surface.

The preferred structure, however, is shown in FIGS. 1 and 2. The pattern for this structure can be prepared by cutting a piece of white, translucent (opal) Plexiglas (or other similar polyacrylic) sheet to the desired size to fit inside a panel. Then the sheet is sagged to the desired shape at about 125° to 150° C, preferably about 135° C, and then slowly cooled. The shaped sheet is mounted on its frame. The pattern is now produced photographically on a piece of web, such as Kodak Type 3 stripping film, marketed by Eastman Kodak Co., Rochester, N. Y., using known photographic methods for the preparation of a high contrast image from a silver halide layer. The photographic master used to make the pattern may be a ruled line pattern that is sold commercially; or it may be a photographic master generated photographically by three offset exposures using the photographic masters that are used for making the shadow masks that are to be used with the particular panels. The web is supported on a hoop and, while it is still wet after photographic development, it is draped over the convex surface of the pedestal 17 and permitted to dry slowly, usually for 1 to 20 hours. The resulting pattern comprises an array of clear light-transmitting lines or dots separated by light opaque areas.

The pattern 39 for the structure shown in FIG. 5 can be made by similar photographic methods except that a photographic linen, for example, Argenta and Luminos photographic linen, marketed by Oscar H. Hirt Co., Reading, Pa., may be substituted for the stripping film mentioned above. This results in a pattern comprising an array of white or light-colored light-reflective lines or dots separated by dark light-absorbing areas. As a result, the plate comprising the pedestal 37 need not have any special optical qualities. However, if a stripping film is used, the pedestal 37 should have a diffuse light-reflecting surface.

Alternatively, the patterns for any of the embodiments may be made by other methods including those methods used for making a matrix on the inner surface of the window. This may include the transfer of a matrix made on the inner concave surface of a panel to the convex surface of a pedestal.

In the structure shown in FIGS. 1 and 2, the upper wall 15 of the light box can be of clear or translucent material; or it can be omitted completely provided other means for supporting the legs 21 and the structure thereon are provided.

We claim:

1. A method for inspecting a glass viewing window for a cathode-ray tube, said viewing window having a light-scattering inner surface, said window to be used for transmitting video images displayed on a luminescent viewing screen within said tube, said video images comprising a repetitive array of video image elements, said method comprising
    (a) providing a pattern of visually contrasting areas, which pattern approximates said array of image elements,
    (b) positioning said pattern adjacent said inner surface of said window,
    (c) observing said pattern through said window,
    (d) and identifying those local regions of said window where said pattern appears distorted.

2. The method defined in claim 1 wherein said pattern comprises an array of light-transmitting and light-opaque areas.

3. The method defined in claim 2 wherein said pattern is positioned against said inner surface, and light from a diffuse source is projected through said light-transmitting parts.

4. The method defined in claim 2 wherein said pattern is a photographic image supported on a transparent film generally conforming in shape to said inner surface.

5. The method defined in claim 1 wherein said pattern comprises an array of light-reflective and light-absorptive areas.

6. The method defined in claim 5 wherein said pattern is positioned against said inner surface and light is projected through said window and reflected by said light-reflective areas back through said window.

7. A method for inspecting a glass viewing window for a cathode-ray tube, said window to be used for transmitting video images displayed on a luminescent viewing screen supported on the inner surface of said window, said inner surface having a stippled light-scattering surface and said viewing screen comprising a regular structure of image elements, said method comprising
    (a) providing a regular pattern of visually contrasting areas in repetitive array, which pattern approximates said structure of image elements,
    (b) positioning said pattern against said inner surface of said window,
    (c) illuminating said pattern,
    (d) scanning said illuminated pattern through said window,
    (e) and identifying those local portions of said window where said pattern appears to differ from being a regular pattern of visually-contrasting parts.

8. The method defined in claim 7 wherein said pattern is a repetitive array of light-transmitting and light-opaque parts which is illuminated by projecting light therethrough towards the means for said observing.

9. The method defined in claim 7 wherein said pattern is a repetitive array of light-reflective and light-absorptive parts which is illuminated by reflecting light from said pattern towards the means for said observing.

* * * * *